United States Patent
Matsumoto

(10) Patent No.: US 9,662,011 B2
(45) Date of Patent: May 30, 2017

(54) OPHTHALMOLOGIC APPARATUS AND METHOD OF CONTROLLING THE SAME

(71) Applicant: CANON KABUSHIKI KAISHA, Tokyo (JP)

(72) Inventor: Kazuhiro Matsumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 67 days.

(21) Appl. No.: 14/526,670

(22) Filed: Oct. 29, 2014

(65) Prior Publication Data

US 2015/0150449 A1 Jun. 4, 2015

(30) Foreign Application Priority Data

Nov. 29, 2013 (JP) ................................. 2013-247286

(51) Int. Cl.
| | |
|---|---|
| A61B 3/14 | (2006.01) |
| A61B 3/00 | (2006.01) |
| A61B 3/10 | (2006.01) |
| A61B 3/12 | (2006.01) |

(52) U.S. Cl.
CPC .......... *A61B 3/1025* (2013.01); *A61B 3/0025* (2013.01); *A61B 3/0058* (2013.01); *A61B 3/0091* (2013.01); *A61B 3/12* (2013.01); *A61B 3/14* (2013.01)

(58) Field of Classification Search
USPC .................................................. 351/206, 246
See application file for complete search history.

(56) References Cited

U.S. PATENT DOCUMENTS

| | | | |
|---|---|---|---|
| 8,235,528 B2 | 8/2012 | Mukai et al. | |
| 8,851,673 B2 | 10/2014 | Hirose | |
| 9,004,684 B2 | 4/2015 | Iwanaga et al. | |
| 2009/0268160 A1 | 10/2009 | Iwanaga et al. | |

(Continued)

FOREIGN PATENT DOCUMENTS

| | | |
|---|---|---|
| CN | 101564286 A | 10/2009 |
| CN | 103251381 A | 8/2013 |

(Continued)

OTHER PUBLICATIONS

Apr. 2, 2015 European Search Report in European Patent Appln. No. 14003818.3.

(Continued)

*Primary Examiner* — Jack Dinh
(74) *Attorney, Agent, or Firm* — Fitzpatrick, Cella, Harper & Scinto

(57) ABSTRACT

Provided is an ophthalmologic apparatus including: a scanning unit for scanning a measuring beam on a fundus of an eye to be inspected; an adjustment unit for performing focus adjustment for a plurality of image acquiring planes provided along an optical axis of the measuring beam projected on the fundus; a correction unit for correcting an aberration generated in the eye; an image acquiring unit for acquiring images for the plurality of image acquiring planes; and a calculation unit for calculating, in correspondence to a diopter of the eye, a focus displacement amount when an image of a first image acquiring plane is obtained and when an image of a second image acquiring plane at a predetermined distance away from the first image acquiring plane in the optical axis direction is obtained. The adjustment unit performs the focus adjustment in accordance with a calculation result in the calculation unit.

23 Claims, 8 Drawing Sheets

(56) References Cited

U.S. PATENT DOCUMENTS

| | | |
|---|---|---|
| 2010/0277692 A1 | 11/2010 | Mukai et al. |
| 2013/0215384 A1 | 8/2013 | Hirose |
| 2013/0215385 A1 | 8/2013 | Hirose |
| 2013/0261612 A1 | 10/2013 | Yokosuka et al. |

FOREIGN PATENT DOCUMENTS

| | | |
|---|---|---|
| EP | 2 395 343 A1 | 12/2011 |
| EP | 2 638 849 A1 | 9/2013 |
| JP | 2010-259543 A | 11/2010 |

OTHER PUBLICATIONS

Dec. 29, 2015 Chinese Official Action in Chinese Patent Appln. No. 201410718104.6.

| DIOPTER (D) | DISPLACEMENT AMOUNT FROM REFERENCE PLANE (μm) | | | | | |
|---|---|---|---|---|---|---|
| | 0 | 60 | 120 | 180 | 240 | 300 |
| -10 | 0.0000 | 0.1434 | 0.2877 | 0.4329 | 0.5789 | 0.7258 |
| -5 | 0.0000 | 0.1744 | 0.3499 | 0.5266 | 0.7044 | 0.8834 |
| 0 | 0.0000 | 0.2083 | 0.4182 | 0.6295 | 0.8423 | 1.0567 |
| 5 | 0.0000 | 0.2453 | 0.4926 | 0.7417 | 0.9928 | 1.2459 |
| 10 | 0.0000 | 0.2854 | 0.5731 | 0.8633 | 1.1559 | 1.4510 |

OPHTHALMOLOGIC APPARATUS AND METHOD OF CONTROLLING THE SAME

BACKGROUND OF THE INVENTION

Field of the Invention

The present invention relates to an ophthalmologic apparatus and a method of controlling the same, and more particularly, to a fundus image acquiring apparatus for acquiring an image of a minute site of a fundus of a subject at high resolution.

Description of the Related Art

There is known a technology for detecting a wavefront aberration of a reflected beam of light projected on a fundus by using a wavefront sensor disposed in a position approximately conjugate with a pupil of an eye to be inspected, and correcting an aberration of the eye to be inspected which is detected as the wavefront aberration by using an aberration correcting device. A research is also made to acquire an image of a minute site of a fundus at high resolution by utilizing the aberration correcting technology, and to use information on shapes and densities of photoreceptor cells, flow of blood cells, run of nerve fiber layers, damage, and the like in diagnosis.

When an image of a fundus is acquired while correcting an aberration, an image having a resolving power of several micrometers is obtained. Because this optical system has a high NA, a depth of field is shallow, and hence the resulting image is limited to information in the range of several tens of micrometers in a depth direction. As a result, a clinical value is high because only an image of an interested layer can be observed. However, a clinically interested tissue within a retina has a gap of about several hundreds of micrometers in the depth direction from a pigment epithelium to a nerve fiber layer. Therefore, in order to observe the tissues, refocus is necessary on the individual tissues or layers. In addition, because stereoscopic information on a thickness of each layer and the like is also useful in the diagnosis, it is also demanded to form three-dimensional imaging information or a three-dimensional image which is displayed with a precise size.

Japanese Patent Application Laid-Open No. 2010-259543 discloses a technology for obtaining three-dimensional information on a subject by using a confocal microscope. Because, with this technology, the stereography is carried out while a stage on which a subject is placed is quantitatively moved with respect to a fixed optical system, precise stereoscopic information is obtained. However, the fundus is required to be imaged through an optical system of the eye ball. Therefore, even when the eye to be inspected as the subject is moved similarly to the case of the technology disclosed in Japanese Patent Application Laid-Open No. 2010-259543, the optical position of the subject cannot be precisely changed. In addition, there is a problem in that, because a refractive error, beat, accommodative microfluctuation, a motion of the head, and the like are added to the eye to be inspected, it is difficult to carry out the stereography having precise dimension information in a depth direction.

SUMMARY OF THE INVENTION

In view of the foregoing, it is therefore an object of the present invention to obtain a stereoscopic fundus image of an eye to be inspected having precise dimension information in a depth direction. In order to achieve the above-mentioned object, according to one embodiment of the present invention, there is provided an ophthalmologic apparatus, including: a scanning unit configured to project and scan a measuring beam on a fundus of an eye to be inspected; an adjustment unit configured to carry out focus adjustment for a plurality of image acquiring planes different in position from one another in a direction of an optical axis of the measuring beam projected on the fundus; an image acquiring unit configured to acquire images for the plurality of image acquiring planes; and a calculation unit configured to calculate, in correspondence to a diopter of the eye to be inspected, a focus displacement amount when an image of a first image acquiring plane in the plurality of image acquiring planes is obtained and when an image of a second image acquiring plane in the plurality of image acquiring planes, which is at a predetermined distance in the direction of the optical axis from the first image acquiring plane, is obtained, the adjustment unit being configured to carry out the focus adjustment in accordance with a calculation result in the calculation unit.

According to one embodiment of the present invention, it is possible to obtain the stereoscopic fundus image of the eye to be inspected having precise dimension information in the depth direction without increasing the size of the apparatus.

Further features of the present invention will become apparent from the following description of exemplary embodiments with reference to the attached drawings.

DESCRIPTION OF THE EMBODIMENTS

Now, embodiments of the present invention are described in detail with reference to the attached drawings. An image of layers constructing the retina of the human being, for example, can be acquired with the apparatus of each of the embodiments.

First Embodiment (Apparatus Structure)

Figure 1:
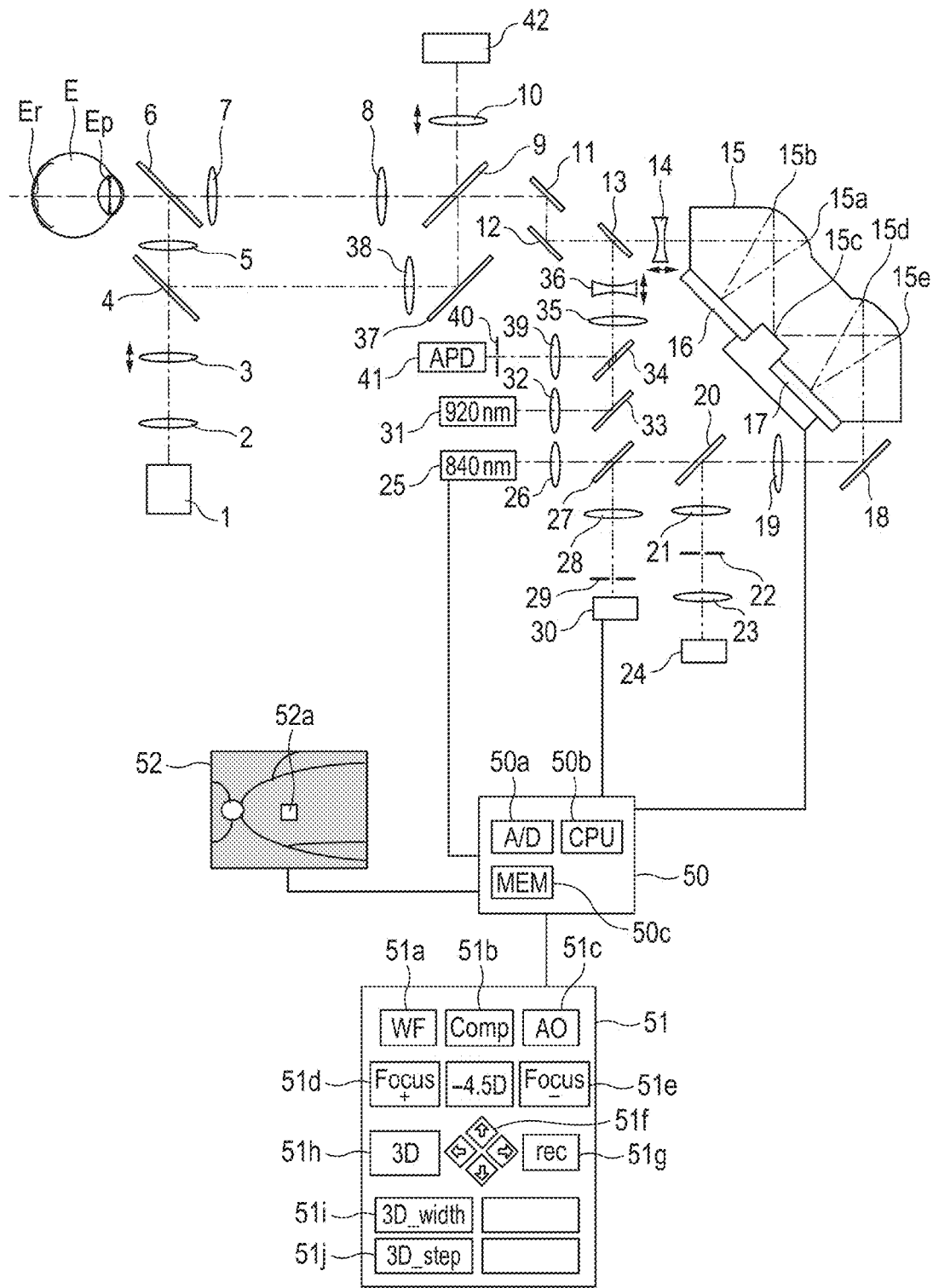
FIG. 1 is a view illustrating a structure of an ophthalmologic image acquiring apparatus according to a first embodiment of the present invention.

A fundus image acquiring apparatus according to a first embodiment of the present invention is now described with reference to FIG. 1.

A light source 1 forms a spot beam for wave front measurement on a fundus. The light source 1 is a laser diode (LD), a light emitting diode (LED), a lamp, or the like, and only needs to have a wavelength that falls within a near infrared range. In the first embodiment, a super luminescent diode (SLD) in which a center wavelength is 760 nm, and a band width of the wavelength is about 20 nm is used as the light source 1. A lens 2 collimates the beams emitted from the light source 1. A focus lens 3 moves on an optical axis, to thereby form an optimal spot image on the fundus of the eye to be inspected. A dichroic mirror 4 has characteristics of transmitting a beam with a wavelength of 760 nm emitted from the light source 1 and reflecting a beam with a wavelength of 920 nm emitted from a light source 31.

A dichroic half mirror 6 has characteristics of reflecting 50% of the beam emitted from the light source 1 and transmitting 50% of the beam emitted from the light source 1, transmitting a beam with a wavelength near 840 nm emitted from a light source 25, and reflecting a beam with a wavelength near 920 nm emitted from the light source 31. The components from the light source 1 to the dichroic half mirror 6 construct an aberration measuring beam projection system. A lens 7 is disposed in such a way that a front focal point position is approximately aligned with a pupil Ep of the eye to be inspected. A lens 8 holds a front focal point position in common with a rear focal point position of the lens 7, and is disposed in such a way that the rear focal point position is aligned with a reflective surface of a high-speed scanning section 12 which is described later. The lens 7 and the lens 8 construct a first pupil imaging optical system.

The dichroic mirror 9 has characteristics of transmitting the beam with the wavelength of the light source 1 and the beam with the wavelength of the light source 25, and reflecting the beam with the wavelength of the light source 31. A lens 10 of a fixation target optical system moves in an optical axis direction and is focus-adjustably disposed. A scanning section 11 such as a galvano scanner carries out sub scan. The high-speed scanning section 12 (meaning to be operated at a higher speed compared to the scanning section 11) such as a galvano scanner, a resonance scanner, or a polygon mirror carries out main scan. Two-dimensional scanning for the beam projected on the fundus is carried out in combination of the main scan and the sub scan by these scanning sections. The scanning sections 11 and 12 correspond to one aspect of a scanning unit configured to project and scan beams with various wavelength bands as measuring beams on the fundus of the eye to be inspected in the first embodiment.

A dichroic mirror 13 has characteristics of reflecting the beam with the wavelength band of 920 nm emitted from the light source 31, and transmitting the beam with the wavelength band of 840 nm emitted from the light source 25. A focus lens 14 moves in the optical axis direction (in the direction indicated by an arrow), to thereby carry out focus adjustment. The focus lens 14 corresponds to one aspect of an adjustment unit configured to carry out focus adjustment for a plurality of image acquiring planes in the optical axis direction of the measuring beam which is projected on the fundus in the first embodiment. A prism block 15 includes free curved surfaces 15a, 15b, 15d, and 15e, and a reflective surface 15c. Aberration correcting devices 16 and 17 each exemplified by a liquid crystal on silicon (LCOS) or a deformabie mirror (DM) are disposed on a side surface of the prism block 15.

The LCOS controls a phase of a beam by utilizing birefringence of liquid crystal molecules, to thereby correct the wavefront of the beam. The orientation of the liquid crystal is determined by the direction of the alignment layer contacting the liquid crystal molecules, and a polarization direction enabling control of the wavefront is determined by the direction of the alignment layer. That is to say, with one LCOS, the wavefront of one of the P polarization component and the S polarization component merely can be corrected. Hence, in order to correct all the wavefronts, it is necessary to use two LCOSs whose directions of the alignment layers are disposed at a right angle with each other. Therefore, the LCOSs 16 and 17 are disposed so that the directions of their alignment layers are at a right angle with each other.

In addition, because the DM can correct the aberration without depending on the polarization, the correction of the aberration can be carried out with one DM. However, an example of using the LCOS is described in the first embodiment because the DM is expensive and the number of divisions thereof is small.

The curved surface 15a of the prism block 15 images the parallel beams transmitted through the lens 14 on the LCOS 16, the curved surface 15b thereof projects an image of a pupil imaged on the LCOS 16 to the infinity, and the curved surface 15e thereof images the image of the pupil on the LCOS 17 again. In addition, the curved surface 15d thereof projects the image of the pupil imaged on the LCOS 17 on the infinity again.

A mirror 18 and a lens 19 are provided. A dichroic mirror 20 has characteristics of reflecting the beam with the wavelength of the aberration measuring light source 1, and transmitting the beam with the wavelength of the light source 25. A lens 21 is provided. A stop 22 is disposed in a position approximately conjugate with the fundus and cuts off the reflected beam from a cornea of the eye to be inspected or the like. A lens 23 is provided. A wavefront aberration detecting device 24 is a Hartmann Shack sensor or the like. The components from the lens 7 to the wavefront aberration detecting device 24 construct an aberration measurement optical system. Hence, the aberration correcting devices 16 and 17, the high-speed scanning section 12, and the wavefront aberration detecting device 24 are disposed to be conjugate with the pupil Ep of the eye to be inspected by these optical systems. These aberration correcting devices 16 and 17 correspond to an aspect of a partial structure of a correction unit configured to correct the aberration generated in the eye to be inspected in the first embodiment.

A half mirror 27 which transmits 10% of the beam and reflects 90% of the beam is disposed in a transmission optical path of the dichroic mirror 20. In addition, a lens 28, a confocal stop 29, and a light receiving element 30 such as a photodiode (PD), an APD, or a PMT are disposed on a reflection optical path of the dichroic mirror 20. Moreover, a lens 26 and the light source 25 are disposed on a transmission optical path of the half mirror 27. As is described later in the first embodiment, the light receiving element 30 constructs one aspect of an image acquiring unit which can acquire images of a plurality of image acquiring planes which are disposed at predetermined intervals in the optical axis direction.

The light source 25 is a light source for AO-SLO for acquiring the image of the fundus at high resolution, and is also an SLD light source for emitting a beam with a wavelength of 840 nm and a half-width of about 50 nm.

Although this light source 25 may be a normal laser or an LD, when an SLD light source with a wide band width is used, an influence of a speckle appearing as a noise on an image can be reduced. The above-mentioned components from the lens 14 to the light receiving element 30, and from the lens 14 to the light source 25 construct a third optical system as a wavefront correction fundus image acquiring optical system (hereinafter referred to as "an AO-SLO optical system") for acquiring an image of a minute site of the fundus at high resolution.

The SLD light source 31 for acquiring a wide angle fundus image emits a beam with a wavelength of 920 nm. A collimator lens 32 and a mirror 33 are provided. A perforated mirror 34 has an opening at a central section thereof. The beam emitted from the light source 31 passes through the opening of the perforated mirror 34, and a return beam from the fundus is reflected by a mirror section in the circumference of the opening. A mirror 35 is provided. A focus lens 36 is disposed controllably so as to move on the optical axis. A mirror 37 and a lens 38 are provided. The lens 38 constructs together with the lens 5 a second pupil imaging optical system. In addition, a lens 39, a confocal stop 40, and a light receiving element 41 such as a photodiode (PD), an APD, or a PMT are disposed in a reflection direction of the perforated mirror 34. The above-mentioned components from the lens 36 to the light source 31, and from the lens 36 to the light receiving element 41 construct a fourth optical system as a wide angle view fundus image acquiring optical system (hereinafter referred to as "a WF-SLO optical system").

In addition, a control circuit 50, an operation panel 51, and a display section 52 are provided. Processing operations of these components 50, 51, and 52 are described later.

(Wide Angle Fundus Image Acquisition)

Next, an image acquiring method using this fundus image acquiring apparatus is described. An operator firstly carries out the rough adjustment of the focus, and the adjustment of the fixation target while the operator observes an image of the fundus of the eye to be inspected, which is acquired at the wide angle.

Firstly, the operator operates a WF switch 51a on the operation panel 51, to thereby select wide angle view image acquisition.

The input to the WF switch 51a is detected by a CPU 50b on the control circuit 50 to turn on the light source 31. As a result, the scanning sections 11 and 12 start to carry out the scanning at an angle for wide angle view image acquisition, and a fixation target presenting section 42 is presented with a fixation target. The beam with the wavelength near 920 nm emitted from the light source 31 is collimated by the lens 32, reflected upward in FIG. 1 by the mirror 33, and passes through the opening section of the perforated mirror 34 to become an approximately parallel beam through the lenses 35 and 36. However, the lens 36 is structured so as to be movable in the optical axis direction (in the direction indicated by an arrow in FIG. 1) for the focus adjustment.

The resulting beam is reflected by the dichroic mirror 13, main-scanned and sub-scanned by the high-speed scanning section 12 and the scanning section 11, respectively, and reflected by the dichroic mirror 9 and the mirror 37 to be imaged in the vicinity of the position of the focal point of the lens 5 by the lens 38. Moreover, the resulting beam is reflected by the dichroic mirror 4, and converted into the parallel beam by the lens 5 to be imaged on the fundus Er through the pupil Ep of the eye to be inspected. A reflected beam from the fundus Er inversely follows the incident optical path again, and is reflected by the mirror section in the circumference of the perforated mirror 34 to be collected on the confocal stop 40 by the lens 39. The beam which has passed through the stop 40 reaches the light receiving element 41 which in turn converts the beam into an electrical signal. The resulting electrical signal is converted into digital data by an A/D converter 50a and is stored in a memory 50c. At the same time, image data is created to be displayed on the display section 52.

(Selection of Image Acquiring Site)

The operator selects an image acquiring site by looking at the image of the fundus displayed on the display section 52. A character 52a showing an area for acquiring an image at high resolution is displayed at a central section of the display section 52. The operator operates a fixation target operation switch 51f so that an interested site on the fundus enters this frame. As a result, an index presentation position on the fixation target presentation section 42 including an LED array, a liquid crystal display, an organic EL display, or the like is changed. An index image formed of the visible light emitted from the fixation target presentation section 42 passes through the lens 10, and is transmitted through the dichroic mirror 9 to be reflected by the mirror 37. The reflected beam is imaged in the vicinity of the position of the focal point of the lens 5 by the lens 38, projected to approximately the infinity by the lens 5, and passes through the pupil Ep of the eye to be inspected to be imaged in the vicinity of the fundus Er.

A subject fixates this index, to thereby guide his/her line of sight, and hence the site of the fundus which is displayed on the display section 52 is moved. The operator continuously operates the fixation target operation switch 51f until the desired site on the fundus enters the character 52a showing the image acquiring area.

(Adjustment of Diopter)

Moreover, the operator operates focus adjusting switches 51d and 51e while the operator looks at the image of the fundus displayed on the display section 52, to thereby control the position of the lens 36 for the focus adjustment. The focus lens 36 of the WF-SLO optical system, the focus lens 14 of the AO-SLO optical system, the focus lens 3 of the aberration measuring beam projection optical system, and the focus lens 10 of the fixation target projection optical system are linked to a linear motion stage whose position can be controlled by a stepping motor (not shown). As a result, the focus lens 36, the focus lens 14, the focus lens 3, and the focus lens 10 can be moved to arbitrary positions, respectively, by inputs of the coordinate data from the CPU 50b to the respective stages.

The CPU 50b which has detected the input to the focus adjusting switches 51d and 51e drives the focus lens 36, the focus lens 3, the focus lens 10, and the focus lens 14 at a rate corresponding to the same diopter in accordance with a coordinate table stored in the memory 50c. As a result, the appropriately same diopter (equal diopter) of the four optical systems can be usually held.

That is to say, in the first embodiment, the fixation unit for allowing the eye to be inspected to fixate, including the fixation target presenting section 42, is included in the image acquiring optical system which includes the light receiving element 30 as the image acquiring element, to thereby adjust a relative positional relationship with the eye to be inspected. In addition, as described above, the fixation unit can carry out the focus adjustment in conjunction with a focus unit of the image acquiring optical system. Note that, as a further aspect of the first embodiment, only the focus lens 10 of the fixation target projection optical system can be driven separately from the lenses or the like used for other focus adjustment. That is to say, an adjusting unit whose one aspect is shown in the first embodiment may carry out the focus adjustment for the image acquiring plane independently of the focus adjustment by the fixation unit. As a result, even when the focus position of the measuring beam is changed, the eye to be inspected can be prevented from attempting to focus on the measuring beam.

(Aberration Measurement)

After completion of the alignment with the eye to be inspected, and the rough adjustment of the focus, the wavefront aberration correction of the eye to be inspected is carried out. The operator operates an aberration correcting switch 51b. The CPU 50b which has detected the input to the aberration correcting switch 51b turns off the light source 31, stops the scanning sections 11 and 12, and turns on the light source 1.

The beam with the wavelength of 760 nm emitted from the light source 1 is collimated by the collimator lens 2, and transmitted through the focus lens 3 and the dichroic mirror 4 to be imaged on the vicinity of the position of the focal point of the lens 5. As a result, the beam emitted from the light source 1 becomes the parallel beam. Then, about half of the beam reflected by the dichroic half mirror 6 enters the pupil Ep of the eye to be inspected to form a spot beam on the retina Er.

This spot beam is reflected by the retina Er, and passes through the pupil Ep of the eye to be inspected again to be transmitted through the dichroic half mirror 6. 50% of the beam which has transmitted through the dichroic half mirror 6 passes through the lens 7 and the lens 8, and transmitted through the dichroic mirror 9 to be reflected by the scanning sections 11 and 12. At this time, the scanning sections 11 and 12 are fixed to the origin positions.

Note that, in order to two-dimensionally scan the fundus, the scanning section 12 is disposed in such a way that the beam reflected by the scanning section 12 is reflected in the direction perpendicular to the drawing sheet. However, the optical axis associated with the scanning section 12 is drawn within the plane so as to be easy to show.

The beam reflected by the scanning sections 11 and 12 is transmitted through the dichroic mirror 13 to enter the prism block 15. The incident beam is reflected by the free curved surface 15a to be reflected by the LCOS 16. The reflected beam is further reflected by the free curved surface 15b, the reflective surface 15c, and the free curved surface 15e to reach the LCOS 17. After the beam has been reflected by the LCOS 17 and is further reflected by the free curved surface 15d, the beam then exits from the prism block 15. A metallic film made of silver, gold, aluminum, or the like is deposited on the above-mentioned free curved surfaces 15a, 15b, 15d, and 15e, and hence the free curved surfaces 15a, 15b, 15d, and 15e reflect the beam.

The beam which has exited from the prism block 15 is reflected by the mirror 18, made into the parallel beam by the lens 19, reflected by the dichroic mirror 20, and condensed on the opening section of the stop 22 by the lens 21 to be imaged on the wavefront aberration detecting device 24 by the lens 23. The wavefront aberration detecting device 24 includes a micro-lens array and an image acquiring element such as a CCD placed on a focal point surface of the micro-lens array. The micro-lens array is disposed so as to be approximately conjugate with the pupil Ep of the eye to be inspected. For this reason, the micro-lens array divides the beam exiting from the pupil Ep of the eye to be inspected into parts for every area, and condenses the resulting beams on the surface of the CCD. The beams thus condensed are read out as image information. Hence, the wavefront aberration of the eye to be inspected can be obtained from information on individual spot positions.

In order to correct the wavefront aberration, the CPU 50b calculates data which is to be input to the LCOSs 16 and 17. The CPU 50b outputs this control information to the LCOSs 16 and 17, to thereby control the wavefront. As a result, the spot position on the wavefront aberration detecting device 24 is corrected, and the wavefront aberration is calculated again. This feedback control ends when a root mean square (RMS) of the wavefront aberration converges so as to be 0.05λ or less.

(AO Image Acquisition)

When the selection of the image acquiring site has been completed in such a manner, the AO-SLO image acquisition for acquiring an image of a minute area at high resolution is carried out. The CPU 50b which has detected the input to an AO image acquiring switch 51c turns off the light source 31, turns on the light source 25, and changes the scanning angles of the scanning sections 11 and 12 to scanning angles each corresponding to image acquiring field angle of the AO-SLO. As a result, the beam with the wavelength near 840 nm emitted from the light source 25 is collimated by the lens 26. Hence, 10% of the resulting beam is transmitted through the half mirror 27.

The beam passes through the dichroic mirror 20 and the lens 19, and reflected by the mirror 18 to enter the prism block 15. Here, in the same manner as that described above, the beam is reflected by the free curved surfaces 15e, 15d, 15b, and 15a, the reflective surface 15c, and the LCOSs 17 and 16 to exit from the prism block 15. As described above, because the LCOSs 16 and 17 modulate the phase of the beam so as to cancel the wavefront aberration of the subject, the aberration of canceling the wavefront aberration of the subject is added to the beam exiting from the prism block 15. The beam concerned is transmitted through the lens 14 and the dichroic mirror 13, and is two-dimensionally scanned by the scanning sections 12 and 11. Next, the beam concerned is transmitted through the dichroic mirror 9, and passes through the lens 8 and the lens 7 to be transmitted through the dichroic half mirror 6, to thereby reach the fundus Er through the pupil Ep of the eye to be inspected.

The beam concerned, for example, is scanned on a minute area having a size of about 0.3 mm×0.3 mm on the fundus Er. In addition, because the aberration of correcting the aberration of the eye to be inspected is added to the beam concerned by the LCOSs 16 and 17, a spot is formed on the fundus Er of the eye to be inspected in a state of being free from the aberration. For example, when a beam diameter of an incident light flux to the pupil Ep is set to a diameter of 4 mm, the spot diameter on the fundus Er is focused to about 5 μm.

The reflected beam from the fundus Er inversely follows the incident optical path, to thereby pass the dichroic half mirror 6, the lens 7, the lens 8, and the dichroic mirror 9. After that, the beam concerned is descanned by the scanning sections 11 and 12 to cancel the scan, and passes through the lens 14 to enter the prism block 15. Then, in the same manner as that described above, the beam concerned is modulated in the phase thereof by the LCOSs 16 and 17 and exits from the prism block 15. Because the wavefront aberration generated from the eye to be inspected is corrected by the LCOSs 16 and 17, the light flux exiting from the prism block 15 becomes the parallel beam whose aberration is corrected.

The resulting light flux is reflected by the mirror 18 to pass through the lens 19, and passes through the dichroic mirror 20. Then, 90% of the beam is reflected by the half mirror 27. The beam after the reflection is condensed on the opening section of the confocal stop 29 by the lens 28. The beam which has transmitted through the confocal stop 29 is received by the light receiving element 30 including a photoelectric conversion device such as a photodiode to be converted into an electrical signal. The resulting electrical signal is input to the control circuit 50, converted into digital data in the A/D conversion section 50a, recorded in the memory 50c, and converted into image data to be displayed on the display section 52.

The operator confirms the image acquiring site and the image quality by looking at the high-resolution image displayed on the display section 52, and carries out the fine correction or the like of the focus by operating the focus adjusting switches 51d and 51e. After that, when there is no problem, the operator operates a recording switch 51g. As a result, the images acquired in a short period of time are recorded as the image data in the memory 50c with a file name being added thereto. The foregoing is the basic image acquiring procedure.

(Relationship Between Subject and Focal Plane)

Figure 2:
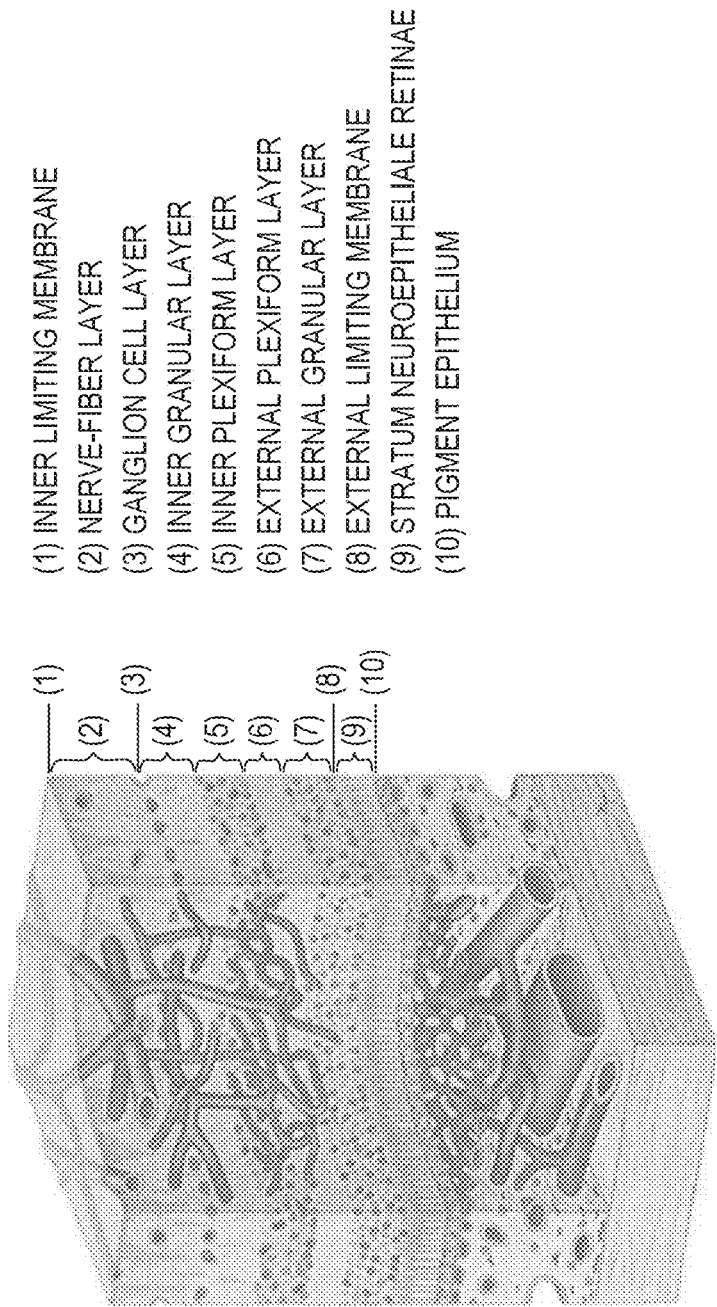
FIG. 2 is a view illustrating a layer structure of a fundus of an eye to be inspected.

Next, a relationship between the retina as the subject, and the focal plane is described. FIG. 2 is a view illustrating a layer structure of the fundus of the eye to be inspected. As illustrated in FIG. 2, the retina includes many layers. The beam emitted from the light source for measurement of the aberration is mostly reflected by a pigment epithelium, and hence focus adjustment is carried out with this plane as a reference. When the stereoscopic information is intended to be obtained, it is preferred that the AO-SLO image be acquired at predetermined intervals in the optical axis, that is, in the depth direction of the fundus with this plane as a reference, and the stereoscopic image be formed based on the image data.

Figures 3, 4:
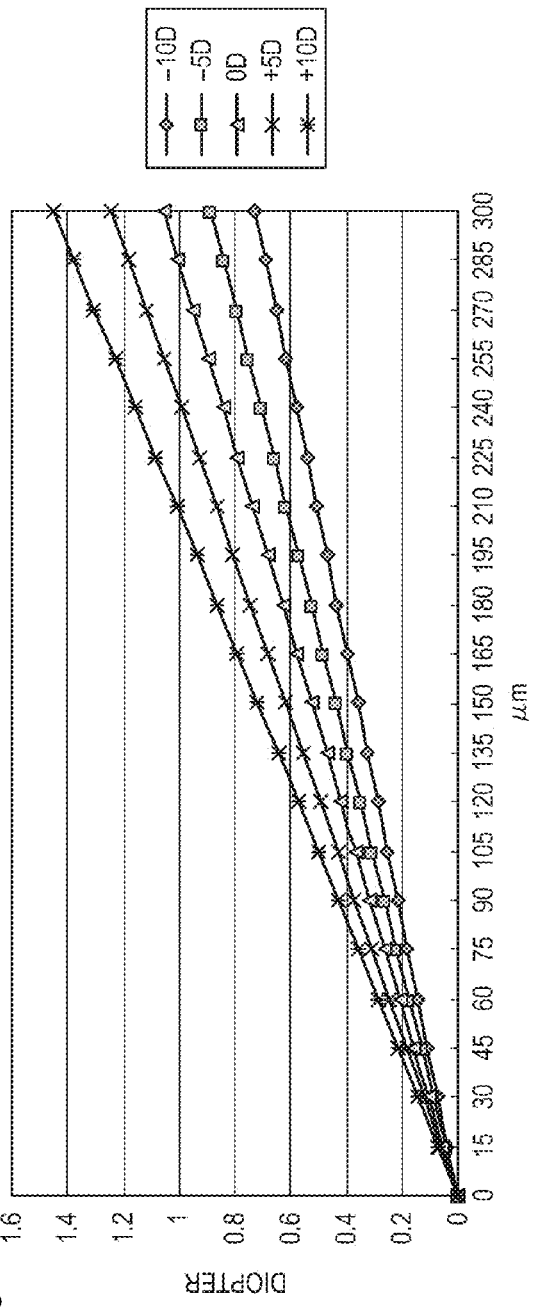
FIG. 3 is a graph showing a relationship between a focus position, and a diopter corresponding to a displacement amount from a reference plane.
FIG. 4 is a table showing main points in the relationship shown in FIG. 3 as numerical values.

FIG. 3 is a graph which shows a focus displacement amount in the form of the diopter when, for example, the image data is obtained at an interval of 15 μm while a focus adjusting mechanism is given a given displacement amount. In FIG. 3, an axis of abscissa represents a distance (focus position) in the optical axis direction, and an axis of ordinate represents the diopter for the reference plane. A plurality of graphs correspond to different diopters of the subject. Actual numeral values in main points of the graph are shown in the table of FIG. 4.

For example, when an image of the site which is at a distance of 120 μm away from the reference plane is intended to be acquired, the focus needs to be changed to 0.2877 D for the subject of −10 D, 0.3499 D for the subject of −5 D, 0.4182 D for the subject of 0 D, 0.4926 D for the subject of +5 D, and 0.5731 D for the subject of +10 D. In addition, when an image of the site which is at a distance of 240 μm away from the reference plane is intended to be acquired, the focus needs to be changed to 0.5789 D for the subject of −10 D, 0.7044 D for the subject of −5 D, 0.8423 D for the subject of 0 D, 0.9928 D for the subject of +5 D, and 1.1559 D for the subject of +10 D.

That is to say, even when images at the positions which are at an equal distance away from the reference plane are intended to be acquired, the displacement amount actually given to the focus adjusting mechanism differs depending on the diopter of the eye to be inspected. Therefore, in order to displace the focal plane with a precise dimension, it is necessary to give the focus adjusting mechanism the different focus displacements depending on the diopter of the subject. In addition, in order to carry out the stereoscopic image acquisition of the displacement amount which is precise in terms of the dimension, the focus adjusting mechanism must be controlled at the different diopter intervals (steps) depending on the diopter of the subject. In order to attain this, a table or a function of an image acquisition interval corresponding to the diopter of the subject needs to be stored in advance.

(Stereography)

Next, details of a procedure when the stereograph is carried out, are described.

Firstly, the operator inputs a range (3D_width) in the depth direction of the stereography and an image acquisition interval (3D_step). Next, the operator carries out the specification of the site to be photographed using the fixation target presenting section 42, and the focus adjustment by the operation of the focus adjusting switches 51d and 51e while the operator observes the image acquired at the wide angle view, which is obtained in the procedure described above. Then, the operator operates a stereography execution switch 51h. As a result, in accordance with the operation of the CPU 50b, the beacon light source 1 emits the beam, and the aberration measuring beam is projected on the fundus of the eye to be inspected. The return beam of the aberration measuring beam is received by the wavefront sensor 24. In addition, the wavefront aberration is calculated from the formed Hartmann image, and coefficients of aberration components are output. The CPU 50b creates a correction image in correspondence to the coefficients of the aberration components thus output, and outputs the data on the correction image to the LCOSs 16 and 17. In addition, an amount (defocus diopter=AO_def) about the defocus of the aberration components is converted into the diopter and the resulting diopter is recorded in the memory 50c.

The CPU 50b calculates the focus displacement amount to be given at the time of the stereography using the defocus diopter AO_def, and adjusts the position of the focus lens. The actual focus lens has such a configuration as to be driven by an actuator which can quantitatively manage the position of a linear motor, a stepping motor, or the like. In addition, data representing the position of the focus lens corresponding to the diopter of the subject is stored in the memory 50c. As a result, controlling the position of the focus lens enables the diopter of the optical system to be set to an arbitrary value.

(Calculation of Focus Displacement Amount)

A description is given of the case of, assuming that the focal length of the eye to be inspected is 17 mm, 3D_width=300 μm, and 3D_step=15 μm, that is, 21 images are acquired while the image acquiring plane is shifted at an interval of 15 μm, to thereby form the stereoscopic image.

The diopter (sub_diop) of the subject can be obtained based on the aberration amount AO_def about the defocus and the focus adjustment amount (WF_diop) obtained by the imaging at the wide angle. The CPU 50b calculates a focus displacement amount Image_diop(k) used to change the image acquiring plane at the stereoscopic image acquiring interval (3D_step) input based on the resulting diopter information. This Image_diop(k) is as follows.

Image_diop(0): the diopter of the subject (=sub_diop)

Image_diop(1): the diopter corresponding to the position which is at 15 μm away from sub_diop Image_diop(k): the diopter corresponding to the position which is at 15×k (μm) away from sub_diop Image_diop(n): the diopter corresponding to the position which is at 15×n=300 (μm) away from sub_diop (where k is an integer of 0≤k≤n)

In addition, a calculation equation for obtaining Image_diop(k) is as described below.

$$\text{Image\_diop}(k) = -(1/f - 1/(\text{back\_}d - 3D\_\text{step} \times k/1000)) \times 1000$$

where back_d=$(1/f+1/(1000/\text{sub\_drop}))^{\wedge}(-1)$, f represents the focal length (17 mm in this case) of the eye of the subject, back_d represents a distance from the eye to the image acquiring plane, and sub_diop represents the diopter of the subject (=AO_def+WF_diop).

The CPU 50b, as described above, calculates the focus displacement amounts for n images and stores the focus displacement amounts for n images in the memory 50c. Firstly, imaging is carried out with Image_diop(0) in accordance with that value. After completion of one imaging, the focus stage is moved to Image_diop(1) in which the imaging is in turn carried out again, and hence n images which are different in focus position are acquired in order, to thereby complete the stereography. In this case, the diopter information (Image_diop(k)) obtained through the image acquisition is also recorded together with the image.

Figure 5:
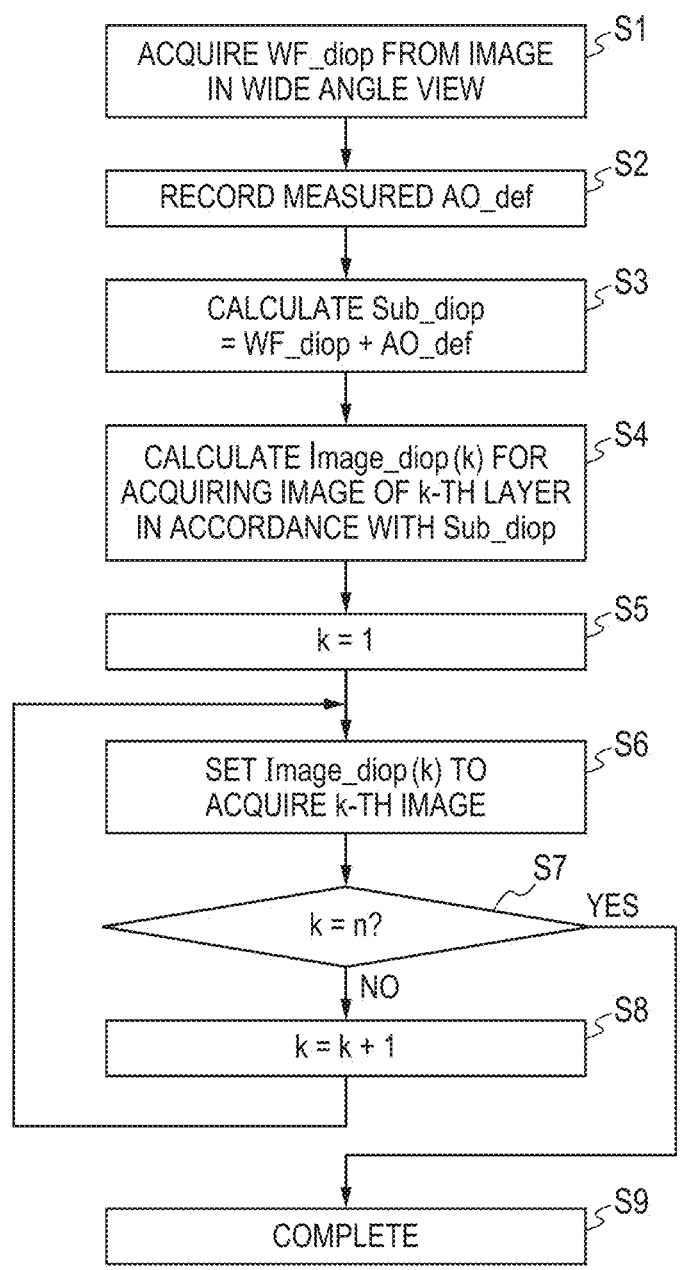
FIG. 5 is a flow chart illustrating flow of an operation for acquiring a stereoscopic image in the first embodiment of the present invention.

The flow of the imaging described above is illustrated in a flow chart of FIG. 5 over again.

In Step S1, the focus adjustment amount (WF_diop) is obtained from the image acquired in advance in wide angle view. In addition, in Step S2, the aberration amount (AO_def) about the defocus obtained in the aberration measurement is recorded. Note that, the order of Step S1 and Step S2 may be reversed. Next, in Step S3, the diopter (sub_diop) of the subject is obtained based on the focus adjustment amount and aberration amount thus obtained, and is then recorded. In Step S4, the diopter (Image_diop(k)) which is used for acquiring an image of a k-th layer corresponding to the diopter information is calculated. After 1 is substituted into k in Step S5, Steps S6 to S8 are repetitively executed while the image acquiring diopter k is increased one by one in order, to thereby acquire a plurality of images. When the n images corresponding to N focus displacement amounts stored in the memory 50c are obtained, the flow proceeds to Step S9, and the stereography ends.

In the operation described above, the displacement amount of focus when the image of the first image acquiring plane of a plurality of image acquiring planes is obtained and when the image of the second image acquiring plane which is at a predetermined distance in the optical axis direction away from the first image acquiring plane is calculated so as to correspond to the diopter of the eye to be inspected. In addition, the above-mentioned focus adjusting unit carries out the focus adjustment in accordance with this calculation result. This calculation is carried out in a functional area in the CPU 50b exemplified as one aspect of a calculation unit in the first embodiment. In addition, the CPU 50b includes a module area as well which functions as a unit configured to acquire the stereoscopic image as the three-dimensional image by, for example, synthesizing the images obtained from a plurality of image acquiring planes, that is, configured to form the three-dimensional image.

In addition, although in the first embodiment, the image acquiring planes are disposed at the arbitrary intervals, or at the predetermined intervals on the optical axis of the measuring beam, these image acquiring planes may also be disposed at predetermined equal intervals. In this case, the calculation unit calculates the focus displacement amounts in correspondence to the change amounts of the diopter when these image acquiring planes are disposed at the predetermined equal intervals. By adopting this structure, although the dimension precision is reduced in terms of the stereoscopic fundus image as a simplex, such effects can be obtained that the comparison is simplified by the standardized form display of a plurality of eyes to be inspected, or the burden imposed on the calculation unit is reduced.

Note that, it is preferred that the image information when the image acquiring plane is displaced from a reference position (a position of a plane in which the pigment epithelium is present in FIG. 2) on the optical axis on which the above-mentioned image acquiring plane is disposed to the image acquiring position where the second image acquiring plane is disposed be recorded together with the information on the distance from the reference position in the above-mentioned memory 50c. In this case, the memory 50c is exemplified as one aspect of a recording unit configured to record therein the distance information together with the image information in the first embodiment. In addition, the display section 52 is exemplified as one aspect of a display unit in the first embodiment which can also display thereon the image information together with the distance information at the time of the display of the resulting image.

(Focus Change by LCOS)

Here, it takes time to acquire the plurality of images described above, and hence a change in the image acquiring site is easy to occur. For this reason, it is desirable to acquire the n images in a short period of time as much as possible. Although the focus displacement for stereoscopic image acquisition may be controlled by moving the position of the focus lens, it takes time to drive and stop the motor for controlling the lens position. Then, when the defocus adjustment of the aberration correcting device is used, the image acquiring time can be shortened rather than other cases because the image acquisition position can be quickly displaced.

In addition, images are not acquired at all the image acquisition positions displaced at the equal intervals, and the image acquiring time can be shortened by skipping any of the relatively less interested portions. In this case, although the image data on the portions skipped on the way is not obtained, the stereoscopic information is not injured because the distances between the imaged portions and the reference position are precisely known.

For the stereoscopic image structured by the images acquired in such a manner, the imaging intervals in the depth direction are calculated based on the diopter of the subject. Therefore, even in the case of the eyes to be inspected corresponding to the different diopters, imaging is possible with the precise displacement amounts, and hence the stereoscopic information having a precise dimension in the depth direction can be obtained. The precise stereoscopic information in the depth direction is significant especially when many subjects are imaged to collect the statistical data. In addition, even when the data on the thinning of the nerve fiber layer and the stratum neuroepitheliale retinae, and the like is compared with the data on the healthy eye to early discover the abnormality, the precise stereoscopic information in the depth direction is significant for the diagnosis because the comparison can be made based on the physical scale.

Although 17 mm is used as the focal length of the eye in the first embodiment described above, because the focal length of the eye to be inspected can be estimated from a value of an eye axis length measured with another instrument and from an abnormal refractive value, the use of that value further enhances the precision.

Second Embodiment

A time required to acquire one image is 40 msec. if, for example, 25 frames are acquired per one second (25 fps). As described above, the movement in the longitudinal direction of the image acquiring plane is carried out between the image acquisition and the image acquisition of each frame, which takes more time. Hence, the time of about 1 sec. to about 3 sec. is required for the imaging of 21 frames. An accommodative microfluctuation of about 0.3 diopter at about 0.6 Hz and at 1 Hz to 2 Hz is present in the eye. This accommodative microfluctuation changes apparently the retina position. Therefore, this accommodative microfluctuation becomes a main factor to cause imprecision in the imaging intervals in the longitudinal direction in the system for carrying out the control with one step as about 0.05 diopter. In addition, the image acquiring plane is changed even by the misalignment of the eye to be inspected caused by a head motion.

Then, in a second embodiment of the present invention, the focus deviation is measured with the wavefront sensor concurrently with the imaging. In addition, unlike the first embodiment, not only the image acquiring plane is moved to the predetermined position in regular order, but also the imaging is carried out while the change in detected diopter is corrected. By adoption of this structure, the enhancement of the precision of the stereoscopic information is further expected. That is to say, in the second embodiment, the aberration correction unit further has the function of the adjusting unit configured to carry out the focus adjustment of the measuring beam.

Figure 6:
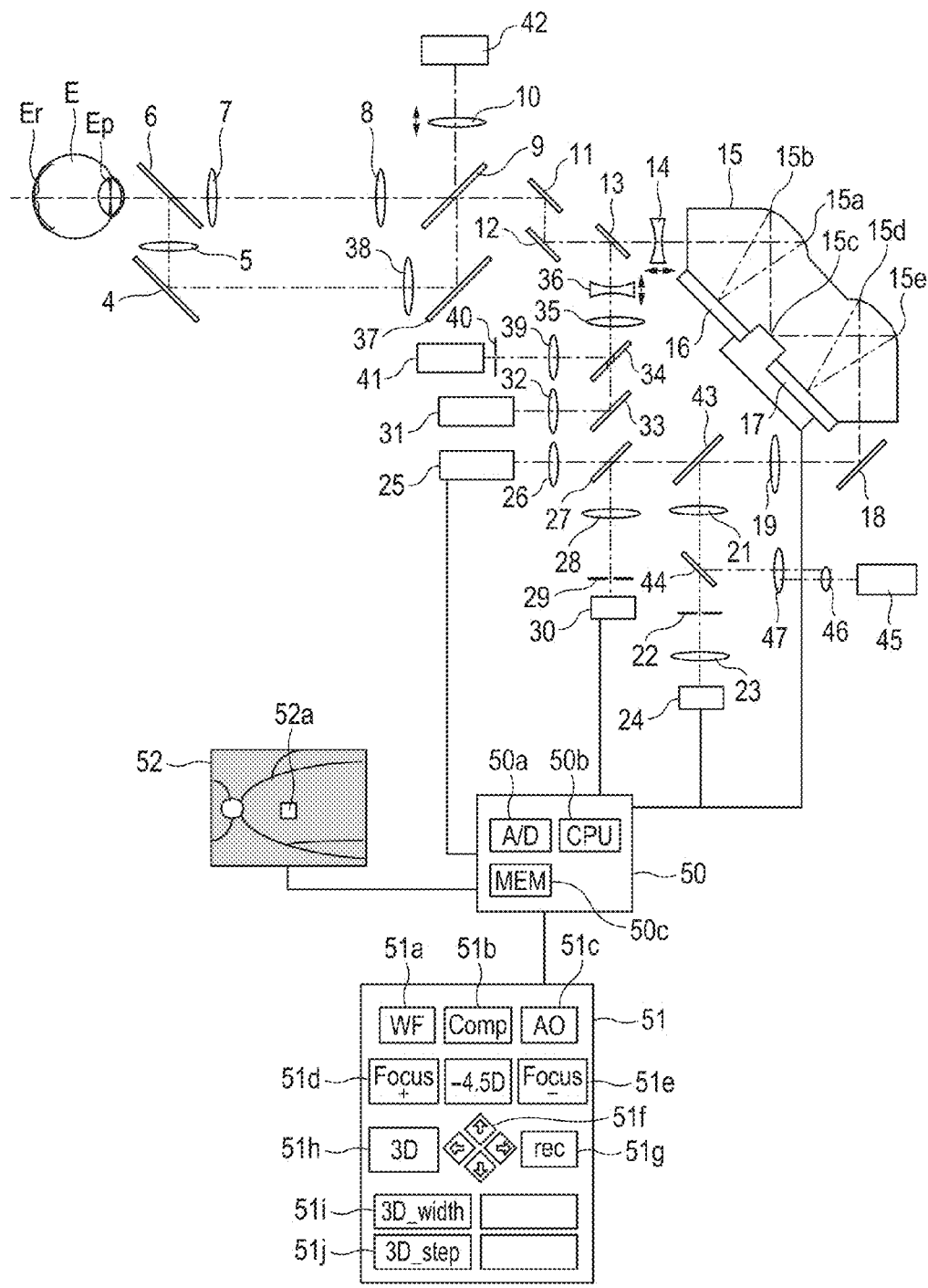
FIG. 6 is a view illustrating a structure of an ophthalmologic image acquiring apparatus according to a second embodiment of the present invention.

FIG. 6 illustrates an example of a structure of an apparatus, using a real time AO system, for carrying out the wavefront aberration measurement concurrently with the imaging.

In the second embodiment, a light source 45 for the aberration measurement, a lens 46, and a lens 47 are disposed in a direction of reflection of a half mirror 44 which reflects 10% of a beam with a wavelength of 760 nm emitted from the light source 45. This half mirror 44 is disposed between the lens 21 and the stop 22. In the second embodiment, the light source 1 for the aberration measurement, and the projection optical system thereof which are illustrated in FIG. 1 are omitted.

With such a structure, 10% of the beam emitted from the light source 45 is reflected by the half mirror 44. This beam is further reflected by a dichroic mirror 43, and subsequently, is two-dimensionally scanned on the retina of the eye to be inspected by the scanning sections 11 and 12 similarly to the case of the first embodiment. The return beam from the fundus Er reversely follows the optical path. 90% of the beam is transmitted through the half mirror 44 to reach the wavefront sensor 24 through the fundus conjugate stop 22.

(Procedure of Image Acquisition)

A procedure of the image acquisition is described with reference to FIG. 6.

Similarly to the case of the first embodiment, firstly, the image of the fundus is acquired at the wide angle to observe the eye to be inspected. The operator operates the focus adjusting switches 51d and 51e so that an observation image becomes brightest while the operator looks at the observation image. It is assumed that as a result of the operation, the brightest image is obtained at −4.5 D (diopter). That is to say, the focus lens 14 is disposed at −4.5 D. An approximate polynomial with which the diopter is converted into the number of steps of the focus stage is stored in the memory 50c in advance. Hence, the position of the focus lens and the diopter can be usually made to correspond to each other.

Next, the beacon light source 45 is caused to emit a beam. The beam emitted from the beacon light source 45 two-dimensionally scans the fundus. The beam diameter of the beacon beam in the pupil of the eye to be inspected is set as narrow as about 1 mm. In addition, the beacon beam passes through the position on the pupil surface which is biased by 1 mm to 1.5 mm from the optical axis. The reason for this is because the reflected beam from the cornea surface of the subject must be prevented from entering as the ghost beam the wavefront sensor. In order to attain this, the optical axis of the lens 46 is disposed so as to be biased with respect to the optical axis of the lens 47. Therefore, the spot diameter on the fundus surface is as large as 20 μm, and the focal point depth is also deep.

The return beam from the fundus reversely follows the optical path. The beam is transmitted through the half mirror 44, and passes through the stop 22 which is disposed so as to be conjugate with the fundus surface to reach the wavefront sensor 24. The stop diameter is set to a size (about double) which has sufficient margin for the beam diameter. The reason for this is because even in a state in which the aberration amount cannot be sufficiently compensated for, that is, the spot beam is not sufficiently focused, the aberration is appropriately measured. The beam concerned is accumulated for one frame, and is then sent to the CPU 50b. In addition, the wavefront aberration is calculated by the CPU 50b, and similarly to the case of the previous first embodiment, the correction image is output to the aberration correcting devices 16 and 17, to thereby correct the aberration. The focus component which is corrected at this time is stored as AO_defocus.

(Acquisition of Stereoscopic Image)

Next, a first image is started to be acquired.

During the image acquisition, in addition to the light source 45, the light source 25 is turned on. The beam emitted from the light source 25 is transmitted through the half mirror 43 similarly to the case of the first embodiment, deflected by the scanning sections 12 and 11 serving as scanning mirrors, transmitted through the dichroic mirror 9 to reach the fundus Er. The reflected beam from the fundus Er reversely follows the optical path to reach the half mirror 27. 95% of the beam is then reflected by the half mirror 27, and passes through the fundus conjugate stop 29 to reach the light receiving element 30 serving as the photoelectric conversion element. The light receiving element 30 converts the intensity of the received beam into an electrical signal which is in turn converted into a digital signal by the A/D board 50a to be stored in the memory 50c.

Concurrently with this, similarly to the foregoing, the reflected beam from the retina of the beam emitted from the beacon light source 45 is accumulated as the Hartmann image in the wavefront sensor 24. The wavefront sensor 24 outputs the Hartmann image as the image data to the memory 50c synchronously with the scanning operation. The CPU 50b analyzes the image data to calculate the aberration. Next, the image data used to correct the detected aberration is created, and output to the wavefront correcting devices 16 and 17 in addition to the last correction image, to thereby carry out the aberration correction again. However, because the second image is to be acquired next time, the focus component used here is set to a value obtained by adding Image_diop(1) to the detected defocus component.

After completion of the above-mentioned setting, the second image is acquired. During this image acquisition as well, similarly to the acquisition of the first image, the wavefront sensor 24 accumulates the Hartmann images. After completion of the acquisition of the second image, the Hartmann image is output as the image data to the memory 50c. The CPU 50b as the calculation unit calculates the remaining wavefront aberration of the eye to be inspected from the image data, creates the correction image, and adds the correction image to the last correction image, to thereby output the resulting data to the LCOSs 16 and 17.

(Focus Detection During Image Acquisition)

The defocus amount detected at this time is Image_diop (1)+diopter change (error_diop) due to variation in eye to be inspected.

Figure 7:
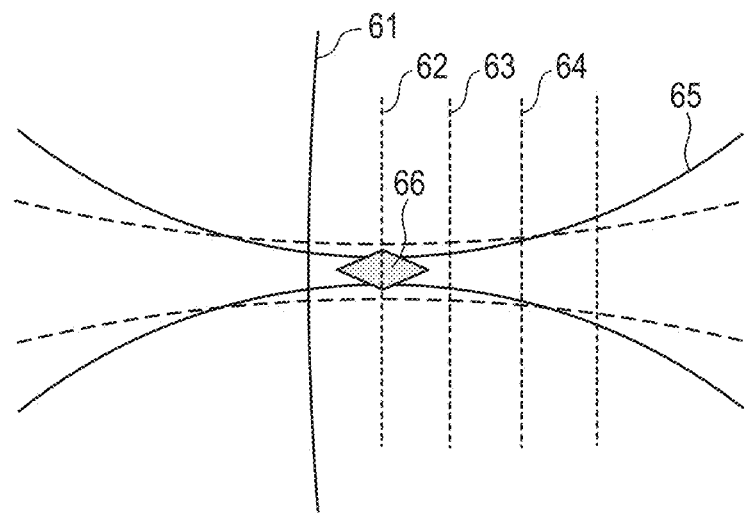
FIG. 7 is a view illustrating an example of an image obtained in the second embodiment of the present invention.
Figure 8:
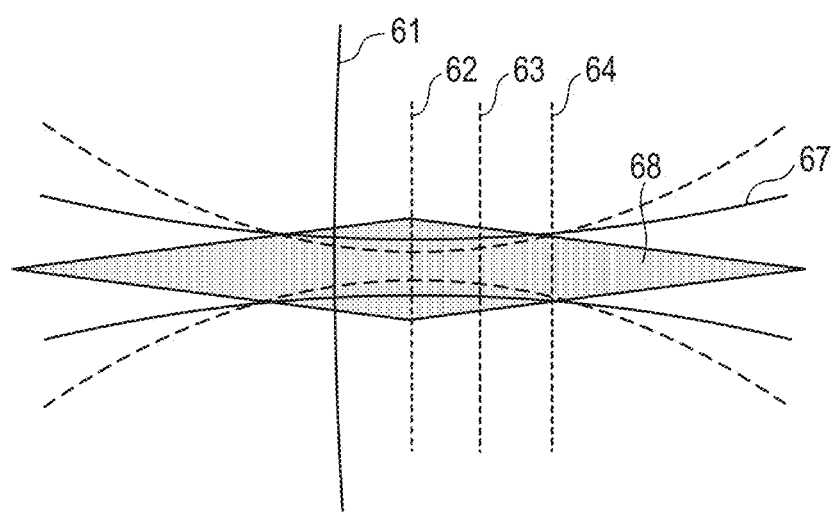
FIG. 8 is a view illustrating another example of the image obtained in the second embodiment of the present invention.

FIG. 7 and FIG. 8 are each a view illustrating a cross section of an image acquiring beam in the vicinity of a pigment epithelium 61. FIG. 7 and FIG. 8 each illustrate a second image acquisition cross section 62 of the stereoscopic image acquisition, a third image acquisition cross section 63 of the stereoscopic image acquisition, and a fourth image acquisition cross section 64 of the stereoscopic image acquisition. In this example, adjacent image acquisition cross sections are 15 μm away from each other. A cross section 65 of the AO-SLO beam illustrated in FIG. 7 has the large ND, and hence the image acquiring range (depth of field) is limited to a narrow area 66. FIG. 8 is a beam cross-sectional view of the beacon beam. In this case, because NA is small and the opening section of the image acquiring stop is large, the image acquiring range is wide, and the beam from a wide area 68 can be received.

Because the pigment epithelium 61 more strongly scatters the beam than other layers, most of the beacon beam projected on the retina is scattered by the pigment epithelium 61. As a result, the return beam from the pigment epithelium 61 is usually dominant for the wavefront sensor 24, and hence the pigment epithelium 61 becomes a reference plane of the focus. A first image of the stereoscopic image acquisition is acquired by focusing on the pigment epithelium 61.

If the wavefront is detected when the first image 61 is acquired, the variation error_diop to the adjustment or motion of the eye to be inspected is detected as the defocus component. Therefore, the detected defocus amount (AO_defocus) is expressed as follows.

$$AO\_defocus + error\_diop$$

Therefore, when the second image 62 is intended to be acquired, the focus position is set as follows.

$$AO\_defocus + Image\_diop(1)$$

If the wavefront is detected while the second image 62 is acquired, a sum of a difference Image_diop(1) between the first image 61 and the second image 62, and the variation error_diop due to the adjustment or motion of the eye to be inspected is detected as the defocus component (AO_defocus).

Therefore, when the detected defocus amount is AO_defocus, a relationship of:

$$AO\_defocus = error\_diop + Image\_diop(1)$$

holds. Therefore, when the third image 63 is intended to be acquired, the focus position is set to as follows.

$$AO\_defocus - Image\_diop(1) + Image\_diop(2)$$

In general, the focus which is set when the k-th image is acquired is as follows.

$$AO\_defocus - Image\_diop(k-2) + Image\_diop(k-1)$$

As described above, the aberration is detected concurrently with the image acquisition and the imaging diopter is determined in consideration of the detected focus deviation. Images of 21 different layers are acquired at equal intervals, and the information on the image acquisition depth (distance) is recorded together with the image information in the memory 50c, to thereby end the stereoscopic image acquisition.

Figure 9:
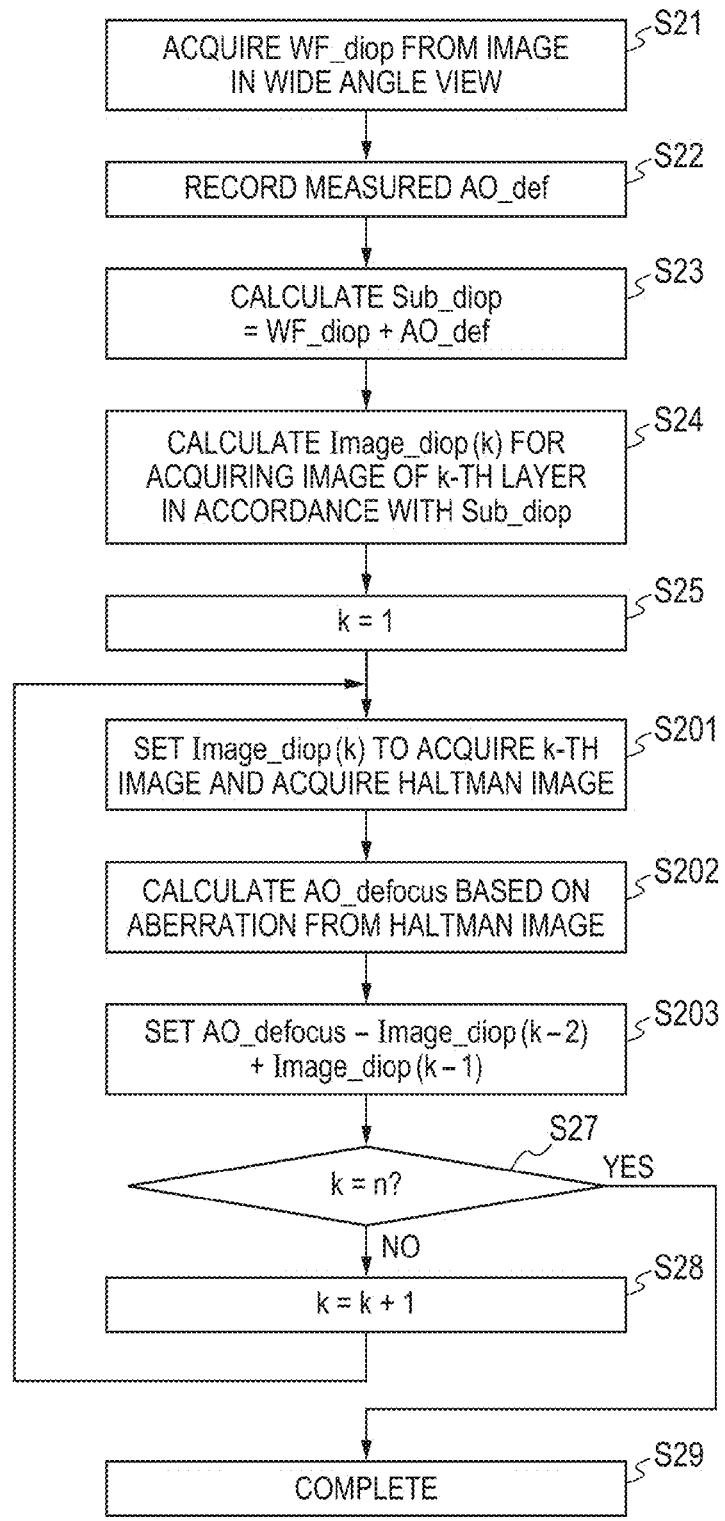
FIG. 9 is a flow chart illustrating flow of an operation for acquiring a stereoscopic image in the second embodiment of the present invention.

The flow of the imaging described so far is illustrated in a flow chart of FIG. 9 over again.

In Step S21, the focus adjustment amount (WF_diop) is obtained from the image acquired in advance in the wide angle view. In addition, in Step S22, the aberration amount (AO_defocus) about the defocus obtained from the aberration measurement is recorded. Note that, the order of Step S21 and Step S22 may be reversed. Next, in Step S23, the diopter (sub_diop) of the subject is obtained based on the resulting focus adjustment amount and aberration amount, and the obtained diopter (sub_diop) of the subject is recorded. In Step S24, the diopter (Image_diop(k)) which is used when the k-th layer corresponding to the diopter information is imaged is calculated. In Step S25, 1 is substituted into k, to thereby obtain the first image. The processes until now are the same as those in Steps S1 to S5 in the first embodiment.

In the second embodiment, after that, the diopter at the time of the image acquisition is set as Image_diop(k), and the image acquisition of the Hartmann image is carried out together with the image acquisition of the layer corresponding to k=1 in Step S201. In Step S202, the defocus amount AO_defocus is calculated by using the aberration amount obtained from the resulting Hartmann image. In Step S203, AO_defocus−Image_diop(k−2)+Image_diop(k−1) is set as the new imaging diopter by referring to the resulting defocus amount. Thereafter, Steps S201 to S203, S27, and S28 are repetitively executed while the imaging diopter k is increased one by one in order, to thereby acquire a plurality of images. When n images corresponding to N focus displacement amounts stored in the memory 50c are obtained, the flow proceeds to Step S29, to thereby end the stereoscopic image acquisition.

Figure 10A:
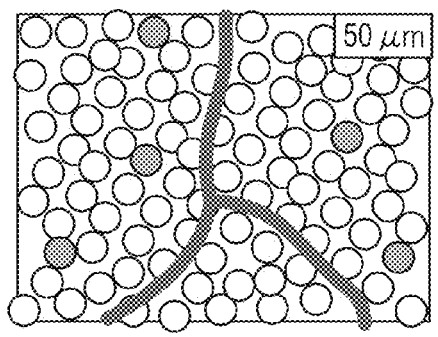
FIG. 10A is a view illustrating an example of an image in the second embodiment of the present invention.
Figure 10B:
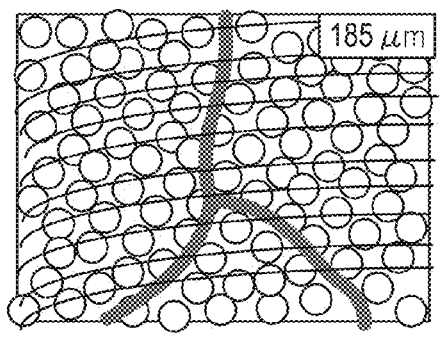
FIG. 10B is a view illustrating another example of the image in the second embodiment of the present invention.

In such a manner, the image acquisition position is also corrected in accordance with the change of the eye to be inspected, to thereby acquire an image which is located at a precise distance from the reference position. Therefore, as illustrated in FIG. 10A or FIG. 10B, the distance from the reference position is shown together with the image. As a result, even when the interested site is imaged in some day in order to observe the progress of the interested site, the image of the site in the same depth direction can be acquired. In addition, the precise physical thickness of each layer can be known from the image after the imaging, which is significant for the medical examination and treatment. Of course, it goes without saying that if such image information is used, the stereoscopic image having the precise size in the depth direction is obtained.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-247286, filed Nov. 29, 2013, which is hereby incorporated by reference herein in its entirety.

What is claimed is:

1. An ophthalmologic apparatus, comprising:
    a scanning unit configured to project and scan a measuring beam on a fundus of an eye to be inspected;
    an adjustment unit configured to carry out focus adjustment for a plurality of image acquiring planes different in position from one another, each of which is perpendicular to an optical axis of the measuring beam projected on the fundus;
    an image acquiring unit configured to acquire images for the plurality of image acquiring planes; and
    a calculation unit configured to calculate, in correspondence to a diopter of the eye to be inspected, a focus displacement amount when an image of a first image acquiring plane in the plurality of image acquiring planes is obtained and when an image of a second image acquiring plane in the plurality of image acquiring planes, which is at a predetermined distance in the direction of the optical axis from the first image acquiring plane, is obtained,
    wherein the adjustment unit is configured to carry out the focus adjustment in accordance with a calculation result in the calculation unit.

2. An ophthalmologic apparatus according to claim 1, further comprising a unit configured to form a three-dimensional image based on the images obtained from the plurality of image acquiring planes.

3. An ophthalmologic apparatus according to claim 1, further comprising a fixation unit configured to allow the eye to be inspected to fixate, the fixation unit being configured to carry out focus adjustment in conjunction with a focusing unit of an image acquiring optical system including the image acquiring unit,
    wherein the adjustment unit carries out the focus adjustment for the plurality of image acquiring planes independently of the focus adjustment by the fixing unit.

4. An ophthalmologic apparatus according to claim 1, further comprising an aberration correction unit configured to correct an aberration generated in the eye to be inspected, the aberration correction unit also having a function of the adjustment unit configured to carry out the focus adjustment of the measuring beam.

5. An ophthalmologic apparatus according to claim 1, wherein when the plurality of image acquiring planes are disposed at equal intervals on the optical axis, the calculation unit calculates the focus displacement amount corresponding to an amount of change in the diopter.

6. An ophthalmologic apparatus according to claim 1, further comprising:
    a recording unit configured to record image information when the image acquiring plane is displaced from a reference position on the optical axis at which the first image acquiring plane is disposed to an image acquiring position on the optical axis at which the second image acquiring plane is disposed together with information on a distance from the reference position; and
    a display unit configured to display the image information together with the information on the distance at a time of display of the image.

7. An ophthalmologic apparatus according to claim 1, further comprising a correction unit configured to correct an aberration generated in the eye to be inspected.

8. An ophthalmologic apparatus, comprising:
    an adjustment unit configured to carry out focus adjustment for a plurality of image acquiring planes different in position from one another, each of which is perpendicular to an optical axis of a measuring beam projected on a fundus of an eye to be inspected;
    an image acquiring unit configured to acquire images for the plurality of image acquiring planes; and
    a calculation unit configured to calculate, in correspondence to a diopter of the eye to be inspected, a focus displacement amount when an image of a first image acquiring plane in the plurality of image acquiring planes is obtained and when an image of a second image acquiring plane in the plurality of image acquiring planes, which is at a predetermined distance in the direction of the optical axis from the first image acquiring plane, is obtained,
    wherein the adjustment unit is configured to carry out the focus adjustment in accordance with a calculation result in the calculation unit.

9. An ophthalmologic apparatus according to claim 8, wherein the adjustment unit configured to carry out the focus adjustment has an aberration correction function of correcting an aberration generated in the eye to be inspected.

10. A method of controlling an ophthalmologic apparatus, the method comprising:
    projecting and scanning a measuring beam on a fundus of an eye to be inspected;
    carrying out focus adjustment for a plurality of image acquiring planes different in position from one another, each of which is perpendicular to an optical axis of the measuring beam projected on the fundus;
    acquiring images for the plurality of image acquiring planes; and
    calculating, in correspondence to a diopter of the eye to be inspected, a focus displacement amount when an image of a first image acquiring plane in the plurality of image acquiring planes is obtained and when an image of a second image acquiring plane in the plurality of image acquiring planes, which is at a predetermined distance in the direction of the optical axis from the first image acquiring plane, is obtained,
    wherein the focus adjustment is carried out in accordance with a calculation result in the calculating.

11. A method of controlling an ophthalmologic apparatus according to claim 10, further comprising forming a three-dimensional image based on the images obtained from the plurality of image acquiring planes.

12. A method of controlling an ophthalmologic apparatus according to claim 10, further comprising allowing the eye to be inspected to fixate while carrying out focus adjustment in conjunction with a focusing unit of an image acquiring optical system including an image acquiring element used in the acquiring images,
wherein the focus adjustment for the plurality of image acquiring planes is carried out independently of the focus adjustment in the allowing the eye to be inspected to fixate.

13. A method of controlling an ophthalmologic apparatus according to claim 10, further correcting an aberration generated in the eye to be inspected, the correcting an aberration being carried out together with the carrying out focus adjustment of the measuring beam.

14. A method of controlling an ophthalmologic apparatus according to claim 10, wherein the calculating comprises calculating, when the plurality of image acquiring planes are disposed at equal intervals on the optical axis, the focus displacement amount corresponding to an amount of change in the diopter.

15. A method of controlling an ophthalmologic apparatus according to claim 10, further comprising:
recording image information when the image acquiring plane is displaced from a reference position on the optical axis at which the first image acquiring plane is disposed to an image acquiring position on the optical axis at which the second image acquiring plane is disposed together with information on a distance from the reference position; and
displaying the image information together with the information on the distance at a time of display of the image.

16. A method of controlling an ophthalmologic apparatus according to claim 10, further comprising correcting an aberration generated in the eye to be inspected.

17. A non-transitory tangible medium having recorded thereon a program for causing a computer to perform steps of the method of controlling an ophthalmologic apparatus according to claim 10.

18. A method of controlling an ophthalmologic apparatus, the method comprising:
projecting and scanning a measuring beam on a fundus of an eye to be inspected;
carrying out focus adjustment for a plurality of image acquiring planes different in position from one another, each of which is perpendicular to an optical axis of the measuring beam projected on the fundus;
correcting an aberration generated in the eye to be inspected;
acquiring images for the plurality of image acquiring planes; and
calculating, in correspondence to a diopter of the eye to be inspected, a focus displacement amount when an image of a first image acquiring plane in the plurality of image acquiring planes is obtained and when an image of a second image acquiring plane in the plurality of image acquiring planes, which is at a predetermined distance in the direction of the optical axis from the first image acquiring plane, is obtained,
wherein the image of the second image acquiring plane is acquired after the focus adjustment is carried out in accordance with a calculation result obtained from the calculating.

19. A method of controlling an ophthalmologic apparatus according to claim 18, wherein the correcting an aberration generated in the eye to be inspected is carried out during the focus adjustment.

20. A non-transitory tangible medium having recorded thereon a program for causing a computer to perform steps of the method of controlling an ophthalmologic apparatus according to claim 18.

21. A method of controlling an ophthalmologic apparatus, the method comprising:
(a) calculating a focus displacement amount in a direction of an optical axis of a measuring beam in correspondence to a diopter of an eye to be inspected;
(b) adjusting a focus position of the measuring beam on a fundus of the eye to be inspected based on the focus displacement amount;
(c) acquiring an image of the fundus of the eye to be inspected, the image being an image of an image acquiring plane which is perpendicular to the optical axis; and
(d) repeating steps (b) and (c), for acquiring a plurality of images of the fundus, the plurality of images being different from each other in the focus position in the direction of the optical axis.

22. A method of controlling an ophthalmologic apparatus according to claim 21, further comprising forming a three-dimensional image based on the plurality of images.

23. A method of controlling an ophthalmologic apparatus according to claim 21, further comprising correcting an aberration having occurred in the eye to be inspected, the correcting an aberration being carried out together with the adjusting focus position of the measuring beam.

* * * * *